United States Patent [19]

Sherlock et al.

[11] 4,029,815

[45] June 14, 1977

[54] ANTI-DIARRHEAL ANTHRANILIC ACIDS

[75] Inventors: Margaret H. Sherlock, Bloomfield; James F. Long, Whippany, both of N.J.

[73] Assignee: Schering Corporation, Kenilworth, N.J.

[22] Filed: Apr. 30, 1975

[21] Appl. No.: 572,981

[52] U.S. Cl. .......................... 424/309; 260/471 R; 260/472; 260/558 A; 260/558 H; 424/319
[51] Int. Cl.² ............... A61K 31/24; C07C 101/54; C07C 103/28; C07C 103/75
[58] Field of Search .................. 424/308, 309, 319; 260/308, 471 R, 472, 558 A, 558 H

[56] References Cited

UNITED STATES PATENTS 3,294,813  12/1966  Juby .................................. 260/465

FOREIGN PATENTS OR APPLICATIONS 14,656  4/1971  Japan .............................. 424/308

*Primary Examiner*—Dale R. Ore
*Attorney, Agent, or Firm*—Raymond A. McDonald; Stephen B. Coan

[57] ABSTRACT

This invention relates to compositions of matter useful as anti-diarrheal agents and to the method of controlling and treating diarrhea in warm blooded animals. The active anti-diarrheal agents are substituted N-arylanthranilic acids, and salts thereof and ester and hydrazine derivatives of said acids.

14 Claims, No Drawings

ANTI-DIARRHEAL ANTHRANILIC ACIDS

It is an object of this invention to provide novel pharmaceutical compositions which will have the effect of controlling and treating diarrhea in warm blooded animals. It is another object of this invention to provide a novel method for the treatment and control of diarrhea in warm blooded animals. Other objects, will also become apparent to those skilled in the art in the light of the instant specification.

It has been found that the objects of this invention may be realized by providing a pharmaceutical composition comprising, as an essential active anti-diarrheal ingredient thereof, a therapeutically effective amount of a compound having the general structual formula:

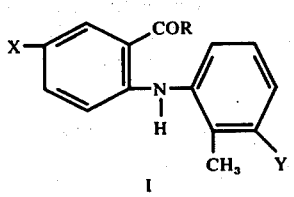

and the pharmaceutically acceptable salts thereof, wherein Y represents trifluoromethyl, difluoromethyl, or nitro, X represents H, chloro, bromo, or nitro and R represents OH, O-lower alkyl,

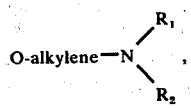

$O-CH_2CHOHCH_2OH$, NHOH or $NR_1NR_2$, wherein $R_1$ and $R_2$ are each hydrogen or lower alkyl.

As used herein the term "lower alkyl", includes those straight and branched chain radicals having up to six carbon atoms, preferably methyl and ethyl. The term "alkylene" embraces a straight or branched chain divalent saturated hydrocarbon having up to six carbon atoms. The preferred salts are the alkali metal salts, and the glyceryl ester is the preferred ester.

The N-aryl anthranilic acids (I) of this invention are prepared by condensing a 2-halo-5X-benzoic acid with the appropriate 2-methyl-3-Y-aniline. In practice, the reaction is conducted in the presence of a copper-containing catalyst and a proton acceptor. In effecting this condensation it is generally satisfactory to employ substantially equivalent quantities of the reactants in the presence of a suitable solvent. Some solvents suitable for this condensation are N,N-dimethylformamide, bis (2-methoxyethyl) ether, dimethyl sulfoxide, nitrobenzene, and lower aliphatic alcohols such as n-butanol, isoamyl alcohol, n-amyl alcohol and the like. The reaction is favored by temperatures in excess of 75° C, preferably in the range of 100° to 200° C, although it is most preferred to effect the condensation at the reflux temperature of the reaction mixture.

Some examples of suitable copper-containing catalysts for this purpose are various forms of mechanically divided or chemically precipitated metallic copper such as e.g. powdered copper or spongy copper and various copper-containing compounds such as cuprous bromide, cuprous chloride, cupric acetate, cupric carbonate, cupric oxide, cupric sulfate and the like. Cupric bromide and cupric acetate are preferred catalysts.

The quantity of the proton acceptor employed in the reaction can be varied within wide limits. In general, the proton acceptor should preferably be added in at least that amount required to bind the benzoic acid reactant and the hydrohalic acid formed in the course of the reaction. Examples of suitable proton acceptors when benzoic acid derivatives of the above formula are employed in free acid form are alkali metal carbonates, preferably potassium carbonate; cupric carbonate, cuprous carbonate and the like. When an alkali metal, and preferably potassium salt of the benzoic acid reactant is employed, calcium hydride, alkali metal carbonates such as e.g. potassium carbonate, and tertiary organic amines such as e.g. N-ethylmorpholine are examples of suitable proton acceptors.

The benzoic acid reactant is advantageously added to the reaction mixture in the form of its preformed alkali metal salt, preferably the potassium salt. Alternatively, the potassium salt of the benzoic acid reactant can be conveniently prepared in situ in a very finely divided condition by adding potassium carbonate to a boiling solution of the free acid form of the corresponding benzoic acid derivative in the solvent employed in the reaction. In the latter case, it is often advantageous to remove most of the water formed in the neutralization by distilling some of the solvent prior to the addition of the catalyst and other reactant. Alternatively, the 2-halo-5-X-benzoic acid reactant may also be in the form of an alkali metal salt or in the form of an ester in which cases the salt or the ester may be removed (by hydrolysis techniques) after the condensation has been effected.

The foregoing condensation reaction may be summarized by the following schematic representation:

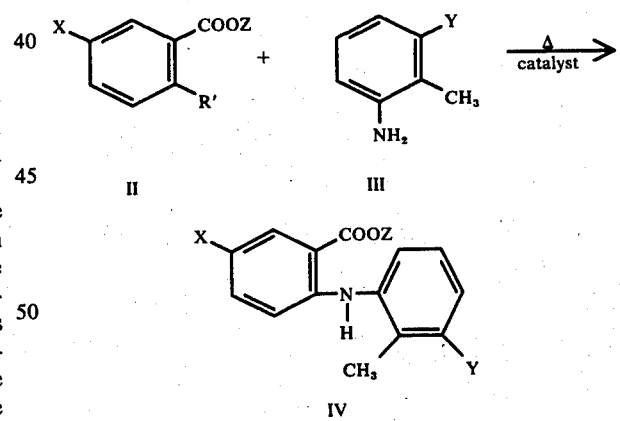

wherein X is hydrogen, nitro or bromo, Z is hydrogen, an alkali metal or a lower alkyl radical, R' is chloro or bromo and Y is trifluoromethyl, difluoromethyl and nitro.

Alternatively, the compounds embraced within this invention may also be prepared by reacting a 5-X-2-amino benzoic acid (or a readily hydrolyzable acid derivative thereof) with an appropriately substituted O-phenyl halide according to standard techniques known in the art.

The compounds of the invention can also be prepared by hydrolysis of an N-acylated anthranilic acid derivative of the formula

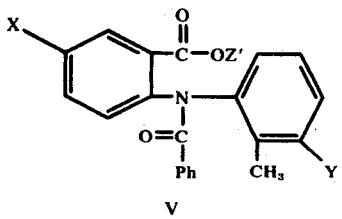

V wherein Z' represents hydrogen or an organic radical such as e.g. lower alkyl and preferably the methyl radical, and Ph represents an aryl radical, preferably phenyl or phenyl optionally substituted by halogen, nitro, lower alkyl, or lower alkoxy groups, and X is hydrogen, nitro or bromo. The hydrolysis is preferably effected in an alkaline medium by dissolving the starting materials in a water-miscible unreactive organic solvent such as ethanol or methanol, adding a large excess of concentrated aqueous solution of sodium or potassium hydroxide and allowing the hydrolysis to proceed (with or without stirring) until the reaction is complete. The hydrolysis is favored by temperatures in excess of 75° C. and is preferably effected at temperatures ranging from 75 ° to about 150° C.

The N-acylated anthranilic acid derivatives of the above formula employed as starting materials in this process can be produced by reacting a benzimidoyl chloride of the formula

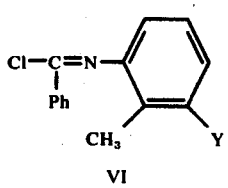

VI with a salicylate of the formula

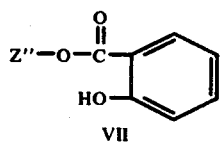

VII or an alkali metal salt thereof to give an imidoester of the formula

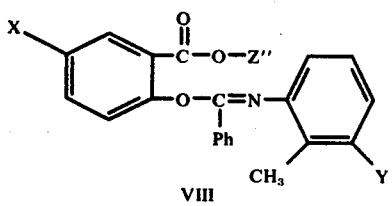

VIII and heating said imidoester to cause an intramolecular rearrangement, optionally subjecting the reaction mixture to mild hydrolysis, preferably in a basic medium, to give the desired N-acylated anthranilic acid derivatives of the above formula. In the above formulae Ph has the hereinbefore mentioned significance and Z" represents an organic radical, preferably lower alkyl.

The condensation of the benzimidoyl chloride with the salicylates or the alkali metal salts thereof is conveniently carried out in a non-reactive solvent medium. In carrying out this reaction it is generally satisfactory to employ substantially equivalent quantities of the reactants. When the salicylate reactant is employed in its free hydroxyl form, the condensation is conducted in the presence of a proton acceptor. The reaction is advantageously carried out in a mixture of ethyl ether and ethanol or methanol in the presence of a base such as e.g. sodium ethylate or sodium methylate. Alternatively, the condensation can be effected in a bis(2-methoxyethyl)-ether medium in the presence of sodium hydride as proton acceptor. The reaction mixture should contain sufficient base to bind the hydrohalic acid formed in the course of the reaction.

The intramolecular rearrangement of the imidoester is favored by temperatures in excess of 150° C. and preferably effected at temperatures ranging from 200° to about 270° C.

The benzimidoyl chlorides of the above formula can be conveniently prepared by reacting an anilide of the formula

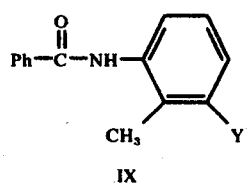

IX with an excess of phosphorous pentachloride at elevated temperatures. The reaction is favored by temperatures ranging from about 80° to about 115° C. In the above formula Ph has the aforementioned significance.

Still another method for preparing those compounds of formula I having either a bromo or a nitro substituent in the 5-position of the benzoid acid moiety is by direct halogenation and nitration procedures, respectively, being effected upon the 5-H-anthranilic acids of formula I.

The glyceryl esters, lower alkanoyl esters, hydrazides, hydroxylamine, dialkylamino, alkyl esters (and the tetrazole analogs thereof) and other such derivatives may be prepared according to standard techniques already well known and taught in this art. Similarly, the alkali and the alkaline earth metal and amine salts of the compounds of this invention may be prepared by methods well known in the art. Representative of such salts are, in addition to sodium, those wherein the cation is ammonium, N-methyl glucamine, diethanolammonium, potassium, lithium, calcium, aluminum and such other metals which advantageously allow for greater solubility or ease in formulation. Exemplary of the teachings by which the anthranilic acids, their esters, salts and other derivatives may be prepared are U.S. Pats. Nos. 3,511,872 and 3,839,344.

The following examples are illustrative of the methods of synthesis of the tangible embodiments of this invention.

EXAMPLE 1

N-(2-Methyl-3-difluoromethylphenyl) anthranilic acid

With constant stirring, reflux a mixture of 11.8 g. of o-chlorobenzoic acid, 25 ml. of n-amyl alcohol, 3 g. of sodium hydroxide pellets, 0.5 g. of copper powder and 17.7 g. of 2-methyl-3-difluoromethyl aniline for 6 hours. Treat the resultant reaction mixture with 3 g. of sodium hydroxide and 0.75 g. of sodium bicarbonate in 25 ml. of water, and remove the unreacted aniline and amyl alcohol by steam distillation. Filter the resulting mixture, acidify with dilute hydrochloric acid and filter the product. Recrystallize the product from acetonitrile to obtain 7.6 g. of N-(2-methyl-3-difluoromethylphenyl) anthranilic acid m.p. 193°–194° C.

EXAMPLE 2

5-Bromo-N-(2-methyl-3-difluoromethylphenyl) anthranilic acid

To a solution of 2.0 g. of cyanomethyl N-(2-methyl-3-difluoromethylphenyl) anthranilate in 100 ml. of carbon tetrachloride add 1.35 g. of N-bromo-succinimide and 20 mg. of benzoyl peroxide. Stir and reflux the reaction mixture under a sun lamp for 2 hours. Cool, filter and recrystallize the product from ethanol to yield 1.7 g. of cyanomethyl-5-bromo-N-(2-methyl-3-difluoromethylphenyl) anthranilate, m.p. 166°–168° C.

A solution of 6.5 g. of the above cyanomethyl ester in 150 ml. of methanol and 50 ml. of 10% potassium hydroxide solution is refluxed for five hours. The reaction mixture is acidified with 10% hydrochloric acid, the product filtered and recrystallized from ether-hexane, to yield 5.2 g. of 5-bromo-N-(2-methyl-3-difluoromethylphenyl) anthranilic acid, m.p. 215°–216° C (dec.)

EXAMPLE 3

5-Bromo-N-(2-methyl-3-trifluoromethylphenyl) anthranilic acid

Over a 30 minute period and with constant stirring, add 16 g. of bromine dissolved in 50 ml. of glacial acetic acid to a mixture of 37 g. of N-(2-methyl-3-trifluoromethylphenyl) anthranilic acid in 350 ml. of glacial acetic acid. Pour the resulting mixture into 1500 ml. of water, filter and dry the precipitate. Recrystallize the product from acetonitrile to obtain 5-bromo-N-(2-methyl-3-trifluoromethylphenyl) anthranilic acid, m.p. 223°–225° C.

EXAMPLE 4

5-Chloro-N-(2-methyl-3-trifluoromethylphenyl) anthranilic acid

To a solution of 25 g. of 2,5-dichlorobenzoic acid in 125 ml. of n-pentyl alcohol add 4.8 g. of sodium hydroxide pellets, 25 g. of 2-methyl-3-trifluoromethylaniline and 2 g. of copper powder. With constant stirring, reflux the reaction mixture for 18 hours. Concentrate the mixture to one half volume and dilute with water and ether. Acidify the aqueous layer to yield the product which is recrystallized from methanol, m.p. 220°–222° C.

EXAMPLE 5

5-Nitro-N-(2-methyl-3-trifluoromethylphenyl) anthranilic acid

To a solution of 25 g. of 2-chloro-5-nitro-benzoic acid in 125 ml. of n-pentyl alcohol add 4.8 g. of sodium hydroxide pellets, 25 g. of 2-methyl-3-trifluoromethylaniline and 2 g. of copper powder. With constant stirring, reflux the reaction mixture for 18 hours. Concentrate the mixture to one half volume and dilute with water and ether. Acidify the aqueous layer to obtain a crude product which is recrystallized to yield 5-nitro-N-(2-methyl-3-trifluoromethylphenyl) anthranilic acid, m.p. 244°–245° C.

EXAMPLE 6

Cyanomethyl N-(2-methyl-3-difluoromethylphenyl) anthranilate

A mixture of 15 g. of N-(2-methyl-3-difluoromethylphenyl) anthranilic acid, 45 ml. of triethylamine and 9 ml. of chloroacetonitrile is stirred and heated on a steam bath for 1¼ hours. The resulting mixture is poured into water and the product filtered. The so-obtained cyanomethyl ester is recrystallized from isopropyl ether to yield cyanomethyl N-(2-methyl-3-difluoromethylphenyl) anthranilate, m.p. 120°–121° C.

In a similar manner by substituting the N-(2-methyl-3-difluoromethylphenyl) anthranilic acid with equivalent quantities of the appropriate anthranilic acids and by substantially following the same procedure of this example, there is produced:

cyanomethyl-5-bromo-N-(2-methyl-3-difluoromethylphenyl) anthranilate,
cyanomethyl-5-nitro-N-(2-methyl-3-difluoromethylphenyl) anthranilate,
cyanomethyl-5-chloro-N-(2-methyl-3-difluoromethylphenyl; anthranilate
cyanomethyl-5-bromo-N-(2-methyl-3-trifluoromethylphenyl) anthranilate,
cyanomethyl-5-nitro-N-(2-methyl-3-trifluoromethylphenyl) anthranilate,
cyanomethyl-5-N-(2-methyl-3-nitrophenyl)anthranilate.

EXAMPLE 7

β-γ-Isopropylidenedioxypropyl-N-(2-methyl-3-difluoromethylphenyl) anthranilate

A mixture of 11 g. of cyanomethyl-N-(2-methyl-3-difluoromethylphenyl) anthranilate, 32 g. of 2,2-dimethyl-1,3-dioxolane-4-methanol and 600 mg. of anhydrous potassium carbonate is heated on a steam bath for 1 hour. The resulting reaction mixture is poured into 500 ml. of water, extracted with ether and the ether layer washed with water several times. The ether extract is dried and concentrated leaving the desired product.

Similarly, by replacing the cyanomethyl-N-(2-methyl-3-difluoromethylphenyl) anthranilate with equivalent quantities of those esters following Example 6, and by substantially following the procedure of this example, there is produced:

β-γ-isopropylidenedioxypropyl-5-bromo-N-(2-methyl-3-difluoromethylphenyl) anthranilate,
β-γ-isopropylidenedioxypropyl-5-nitro-N-(2-methyl-3-difluoromethylphenyl) anthranilate,
β-γ-isopropylidenedioxypropyl-5-chloro-N-(2-methyl-3-difluoromethylphenyl) anthranilate,
β-γ-isopropylidenedioxypropyl-5-bromo-N-(2-methyl-3-trifluoromethylphenyl) anthranilate,
β-γ-isopropylidenedioxypropyl-5-nitro-N-(2-methyl-3-trifluoromethylphenyl) anthranilate,
β-γ-isopropylidenedioxypropyl-5-bromo-N-(2-methyl-3-nitrophenyl) anthranilate.

EXAMPLE 8

Glyceryl-N-(2-methyl-3-difluoromethylphenyl) anthranilate

A solution of 12.6 g. of β-γ-isopropylidenedioxypropyl-N-(2-methyl-3-difluoromethylphenyl) anthranilate and 90 ml. of 75% acetic acid is heated for 30 minutes on a steam bath. The solution is poured on ice, neutralized with cold dilute sodium hydroxide solution, extracted with ether and the ether layer separated, dried and concentrated. Crystallization from ether hexane yields the desired product, m.p. 120°–121° C.

In a similar manner, by substituting β-γ-isopropylidenedioxypropyl-N-(2-methyl-3-difluoromethylphenyl) anthranilate with equivalent quantities of those β-γ-isopropylidenedioxypropyl esters following Example 7 and by substantially following the procedure of this example, there is produced:

glyceryl-5-bromo-N-(2-methyl-3-difluoromethylphenyl) anthraniliate,
glyceryl-5-nitro-N-(2-methyl-3-difluoromethylphenyl) anthranilate,
glyceryl-5-chloro-N-(2-methyl-3-difluoromethylphenyl) anthranilate,
glyceryl-5-bromo-N-(2-methyl-3-trifluoromethylphenyl) anthranilate,
glyceryl-5-nitro-N-(2-methyl-3-trifluoromethylphenyl) anthranilate,
glyceryl-5-bromo-N-(2-methyl-3-nitrophenyl) anthranilate.

EXAMPLE 9

5-Bromo-N-(2-methyl-3-trifluoromethylphenyl) anthranilic acid hydrazide

A solution of 2.1g of cyanomethyl 2-[2-methyl-3-trifluoromethylphenylamino]-5-bromo benzoate and 20 ml. of 98% hydrazine hydrate was heated reflux for 2 hours. The reaction mixture was concentrated to half volume, poured on ice and water and the product filtered. Recrystallization from ethanol-water yielded the hydrazide, m.p. 124°–126° C. Other alkyl hydrazide may similarly be prepared as well as hydrazides of the other anthranilic acids of formula I.

Similarly, the lower alkanoyl esters, the dialkylaminoalkyl esters, aminoalkyl esters, and salts embraced by this invention may be prepared by the techniques well known in the art.

As stated above, the method for treating and controlling acute and chronic diarrheal conditions in warm blooded animals characterized by the secretion of water and electrolytes by the small intestine is effected by administering a therapeutically effective quantity of an anthranilic acid of the structural formula I above, including the salts, esters and other derivatives (i.e. those which are readily hydrolyzable back to the free acid), which have been described hereinabove. The therapeutically effective quantity of a compound of this invention may readily be ascertained by standard and well-known techniques in the art. In testing for the anti-diarrheal activity the compounds are first tested in the rat castor oil/diarrhea model (i.e. the test wherein castor oil is the diarrhea-causing agent). Anti-diarrheal activity is then confirmed by measuring the anti-secretory activity in more sophisticated procedures such as cholera toxin and ricinoleic acid/bile salt-challenged secretion in intestinal loops of dogs.

Accordingly, from the foregoing test procedures, as well as by other standard laboratory techniques, as well as by comparison with well-known anti-diarrheal compositions, it has been found that the compounds of this invention reduce the water/electrolyte secretion, are non-constipating and exhibit a reasonable separation between therapeutic and untoward side-effect doses. Thus, from these tests a therapeutically effective dosage range for the compounds of this invention is from 0.1 mg./kg. to about 40 mg./kg. of body weight. Although it is expected that a therapeutically effective dosage may be administered once a day, dosaging may take place three times daily. Of course, the actual total daily dosage will depend upon the severity of the diarrheal condition, its cause and other health factors of the animal being treated. Thus, in each instance the attending diagnostician will determine the dosage frequency and strength. In practice, the anti-diarrheal compounds of this invention may be administered orally and parenterally; intraveneous administration being effective in more extremely severe and acute conditions, such as in the treatment of colitis in equines and bovines.

In their effect in reversing fluid and electrolyte secretion it is expected that not only will the compounds of this invention control and treat "simple" diarrhea but also that the compounds will be effective in treating diarrhea caused by cholera and other bacterial infestations (e.g. *Escherichia coli*), as well as the treatment and control of diarrhea caused by androgenous intestinal secretogauges (e.g. certain gastrointestinal hormones). Indeed, although cholera is somewhat self-limiting and cure depends upon fluid replacement, a drug treatment (such as by the compounds of this invention) aimed at inhibiting secretion would be invaluable in the practical management of large numbers of cholera victims in an underdeveloped environment.

Additionally, of specific value is the use of the compounds of this invention in veterinary medicine. For example, scours in piglets may be controlled by the administration of the compounds of this invention. Also the compounds find value in the treatment of colitis in horses, and cows, particularly when they have been inflicted with Colitis X. In such instances a very effective dosage is 1 mg./kg. of body weight administered intravenously as quickly after the first symptoms of colitis appears.

As is true for most classes of compounds useful in the treatment of physiological disorders, not all members are equipotent. From the above described laboratory techinques utilized in determining the anti-diarrheal activity of the compounds of this invention, it is determined that, in general, those N-aryl anthranilic acids having the Y-substituent representative of trifluoromethyl or difluoromethyl are particularly useful and those having a 5-position-X-substituent representative of hydrogen or bromo are particularly effective. Particularly effective are those compounds when they are administered in the form of their glyceryl ester or in the form of their N-methyl glucamine salt. Specifically preferred compounds are 2,3-dihydroxypropyl-5-bromo-N-(2-methyl-3-trifluoromethylphenyl) anthranilate, glyceryl ester of N-(2-methyl-3-difluoromethylphenyl) anthranilic acid and the N-methylglucamine salt of 5-bromo-N-(2-methyl-3-trifluoromethylphenyl) anthranilic acid.

The anti-diarrheal agents of this invention can be administered as such, or can be administered in the form of a composition comprising the active ingredient and any of the commonly used pharmaceutical carriers. These carriers must be compatible with the active ingredient, and can be either solid or liquid, therapeutically active or inert. By using such carriers, one can make these compositions in the form of tablets, capsules, powders, oral suspensions, or syrups. The compositions can also be made in the form of sterile solutions which are suitable for injection. The compositions will contain from 1 to 95% by weight of active compound, and from 5 to 99% by weight of a suitable pharmaceutical carrier. These ranges, however, are not critical and can be varied as desired according to the circumstances.

A sterile solution suitable for injection is prepared by admixing from 0.5 to 5 parts by weight of the active ingredient, preferably in the form of its N-methyl-D-glucamine salt, and from 95 to 99.5 parts by weight of water or isotonic saline solution at a temperature and for time sufficient to dissolve the active ingredient. This solution is then sterilized by filtration or by the application of heat. The solution is preferably sterilized in an autoclave at a steam pressure of 15 pounds per square inch for from 5 to 15 minutes. A preferred solution for injection also contains preservatives such as a mixture of methyl- and propylaparaben benzoic acid, or other nontoxic antimicrobial agents.

These injectable solutions can be prepared with a high concentration of active ingredient. The solution is diluted to a desired concentration before it is used.

The compounds of Formula I can also be administered in the form of hard or soft gelatin capsules. These capsules are filled with the proper amount of active ingredient and a solid filler, such as starch, gelatin, lactose, talc, stearic acid, or magnesium stearate. Such a capsule can contain from 50 to 250 milligrams of active material, thus providing a minimum does of active ingredient in a form convenient for oral administration.

The compounds of Formula I, when mixed with a suitable carrier, can also be formulated as tablets. Such carriers must be compatible with the active ingredient and can be the carriers mentioned for use with capsules, or can be such binders or fillers as cornstarch, acacia, gelatin, or cellulosic materials. Generally, any of the tableting materials conventionally used in pharmaceutical practice can be employed if there is no incompatibility with the active ingredient.

The tablets are made by admixing the active ingredient, a suitable filler, a lubricant or mold-release agent, and a binder, and compressing the mixture in a conventional tableting machine into tablets of a preselected size. Preferably, each tablet will contain from 50 to 250 milligrams of active ingredient. The tablets can be scored so that they are easily broken. Optionally, the tablets can be coated with tablet-coating materials, in order to make them more attractive and palatable. They can also have enteric coatings so that they will release their ingredients slowly and over a longer period.

The compounds of Formula I can also be formulated and administered as suspensions or syrups. The anti-diarrheal compound is usually present in such suspensions and syrups in amounts of from 1 to 5% by weight, however, lower or higher concentrations can be used.

The pharmaceutical carrier in such suspensions or syrups can be an aqueous vehicle such as an aromatic water, a syrup, or a pharmaceutical mucilage. Suitable aromatic waters include the following: Anise Water, N.F. (IX); Bitter Almond Water, N.F. (VIII); Camphor Water, N.F.; Cinnamon Water, U.S.P.; Fennel Water, N.F.; Peppermint Water, U.S.P.; Spearmint Water, N.F. (IX); Wintergreen Water, N.F. (IX). Suitable syrups include the following: Syrup (Simple Syrup), U.S.P.; Acacia Syrup, U.S.P.; Aromatic Eriodictyon Syrup, N.F.; Aromatic Rhubarb Syrup, N.F. (IX); Cacao Syrup, U.S.P.; Cherry Syrup, U.S.P.; Cinnamon Syrup, N.F. (IX); Citric Acid Syrup, U.S.P.; Compound Sarsparilla Syrup, N.F.; Compound White Pine Syrup, N.F.; Ginger Syrup, N.F. (IX); Glycyrrhiza (Licorice) Syrup, U.S.P.; Orange Syrup U.S.P.; Orange Flower Syrup, N.F.; Raspberry Syrup, U.S.P.; Rhubarb Syrup, N.F. (IX); Tolu Balsam Syrup, U.S.P.; Wild Cherry Syrup, U.S.P. Suitable pharmaceutical mucilage include the following: Acacia (Gum Arabic), U.S.P.; Acacia Mucilage, U.S.P.; Tragacanth, U.S.P.; Tragacanth Mucilage, N.F. The pharmaceutical carrier in the suspensions or syrups can also be a hydroalcoholic vehicle, such as an elixir. Suitable elixirs include the following: Aromatic Elixir, U.S.P.; Red Aromatic Elixir, N.F.; Glycyrrhiza Elixir, N.F.; Iso-Alcoholic Elixir (Iso-Elixir), N.F. Coloring agents, tinctures, spirts and other adjuvants can be admixed with the composition if desired.

Typical formulations incorporating the anti-diarrheal agents of Formula I are described below. These formulations are intended to be illustrative merely and no limitation is implied or intended.

TABLET FORMULATION

| Formula: | Grams per 1000 Tablets |
|---|---|
| 2,3-Dihydroxypropyl-5-bromo-N-(2-methyl-3-trifluoromethylphenyl)anthranilate | 200.0 |
| Lactose | 90.0 |
| Dicalcium phosphate, hydrous | 122.5 |
| Polyvinylpyrrolidone | 25.0 |
| Polyvinylglycol 1500 | 7.5 |
| Corn Starch | 50.0 |
| Magnesium stearate | 5.0 |
| | 500.0 |

Mix the 2, 3-dihydroxypropyl-5-bromo-N-(2-methyl-3-trifluoromethylphenyl) anthranilate, the lactose and the dicalcium phosphate. Dissolve the polyethylene glycol 1500 and the polyvinylpyrrolidone in approximately 20 ml. of water. Granulate the powder blend with the water solution, adding additional water, if necessary, to produce a damp mass. Pass the wet granulation through a 12 mesh screen; spread on trays and air dry at 35° C. Blend the dry granules with the starch and the magnesium stearate. Compress into 500 mg. tablets.

CAPSULE FORMULATION

| Formula: | Grams per 1000 Capsules |
|---|---|
| 5-Bromo-N-(2-methyl-3-trifluoromethylphenyl) anthranilic acid | 200.0 |
| Lactose | 198.0 |
| Magnesium stearate | 2.0 |
| | 400.0 |

Blend the ingredients and fill into hard gelatin capsules.

ELIXIR FORMULATION

Formula:
5-Bromo-N-(2-methyl-3-trifluoromethyl-

ELIXIR FORMULATION -continued

Formula:
  phenyl) anthranilic acid N-methyl-
    glucamine salt

| | grams per 1000 liters | 40.0 |
|---|---|---|
| Sugar | " | 500.0 |
| Glycerin | " | 200.0 |
| Compound orange spirit | ml | 10.0 |
| Alcohol | ml | 100.0 |
| Amaranth | ml. | 0.1 |
| Water, q.s. 1000.0 ml. | | |

Dissolve the 5-bromo-N-(2-methyl-3-trifluoromethylphenyl) anthranilic acid in the form of its N-methyl-D-glucamine salt, the sugar, the glycerin and the amaranth successively in approximately 400 ml. of water with the aid of heat. Cool the solution to room temperature. Dissolve the compound orange spirit in the alcohol and add the alcoholic solution to the elixir base. Add sufficient water to make the product measure 1000 ml. and agitate until homogeneous. Clarify the elixir by passing it through an asbestos pad, using a filter aid, if necessary.

INJECTION FORMULATION

| Formula: | Grams per 1000 ampuls |
|---|---|
| 5-Bromo-N-(2-methyl-3-trifluoromethylphenyl) anthranilic acid, micronized | 110.0 |
| Water for injection, q.s. 1100.0 ml. | |

Dissolve the 5-bromo-N-(2-methyl-3-trifluoromethylphenyl) anthranilic acid in the form of its N-methyl glucamine salt in the water for injection. Pass the solution through a sterile 0.45 micron membrane filter. Fill asceptically into ampuls (1.1 ml. per ampul). Autoclave the sealed ampuls for 30 minutes under 20 p.s.i.g. steam pressure.

TABLET FORMULATION

I. Formula and method of manufacture for 2,3-dihydroxypropyl-5-bromo-N-(2-methyl-3-trifluoromethylphenyl) anthranilate. Enteric coated tablets:

| Formula: | Mg/core |
|---|---|
| 2,3-Dihydroxypropyl-5-bromo-N-(2-methyl-3-trifluoromethylphenyl) anthranilate | 100.0 |
| Citric acid | 1.0 |
| Lactose, U.S.P. | 33.5 |
| Dicalcium phosphate | 70.0 |
| Pluronic F-68 | 30.0 |
| Sodium lauryl sulfate | 15.0 |
| Polyvinylpyrrolidone | 15.0 |
| Carbowax 1500 | 4.5 |
| Carbowax 6000 | 45.0 |
| 3A alcohol, 50 ml./1000 cores. | |
| Corn starch | 30.0 |
| Dry: | |
| Sodium lauryl sulfate | 3.0 |
| Magnesium stearate | 3.0 |
| Tablet weight | 350.0 |

Procedure

The 2,3-dihydroxypropyl-5-bromo-N-(2-methyl-3-trifluoromethylphenyl) anthranilate is mixed with the citric acid, lactose, dicalcium, phosphate, Pluronic and sodium lauryl sulfate. The above mixture is screened through a No. 60 screen and damp granulated with an alcoholic solution consisting of polyvinylpyrrolidone, Carbowax 1500 and 6000. Add additional alcohol, if necessary, to bring powders to a pasty mass. Add corn starch and continue mixing until uniform granules are formed. Pass through a No. 10 screen, tray and dry in oven at 100° C for 12–14 hours. Reduce dried granulation through a No. 16 screen add sodium lauryl sulfate and magnesium sulfate, mix and compress into desired shape on a tablet machine.

Pluronic F-68 is a U.S. registered trademark for a non-ionic surface-active agent prepared by the addition of ethylene oxide to a polypropylene glycol which has a molecular weight of 1750.

Coating

The above cores are treated with a lacquer and dusted with talc to prevent moisture adsorption. Subcoat layers are added to round out the core. A sufficient number of lacquer coats are applied to make the core enteric. Additional sub-coats and smoothing coats are applied to completely round out and smooth the tablet. Color coats are applied until desired shade is obtained. After drying the coated tablets are polished to give the tablets an even gloss.

(II) Capsule Formulations

| Formula: | Mg./Capsule |
|---|---|
| 2,3-Dihydroxypropyl-5-bromo-N-(2-methyl-3-trifluoromethylphenyl) anthranilate, micronized | 100.00 |
| Citric acid | 1.00 |
| Pluronic, F-68 | 40.00 |
| Sodium lauryl sulfate | 20.00 |
| Lactose | 238.00 |
| Magnesium stearate | 101.00 |
| | 500.00 |

Procedure

Mix together 2,3-dihydroxypropyl-5-bromo-N-(2-methyl-3-trifluoromethylphenyl) anthranilate, citric acid, Pluronic, sodium lauryl sulfate and lactose. Pass through a No. 80 screen. Add magnesium stearate, mix and encapsulate into the proper size 2 piece gelatin capsule.

III ORAL SUSPENSION

Formula:
  2,3-Dihydroxypropyl-5-bromo-N-(2-methyl-3-trifluoromethylphenyl) anthranilate, micronized - 100.0 mg./5 ml.
  Veegum, Vanderbilt — 50.0 mg./5 ml.
  Standard granulated sugar, U.S.P. — 2500.0 mg./5 ml.
  Sorbitol solution, U.S.P. — 1250.0 mg./5 ml.
  Sodium saccharin, NF — 50.0 mg./5 ml.
  Sodium benzoate, U.S.P. — 5.0 mg./5 ml.
  Ethanol, U.S.P. — 0.025 ml.
  Menthol, U.S.P. — 1.000 mg./5 ml.
  Flavor q.s.
  Purified Water, U.S.P., to make 5 ml.

Method of Preparation

Dissolve the sodium saccharin, sodium benzoate, standard granulated sugar and sorbitol solution in approximately 80% of the required amount of water. Disperse the Veegum in approximately 5% of the required amount of water and add the dispersion to the previously prepared syrup. Prepare a slurry of the 2,3-dihydroxypropyl-5-bromo-N-(2-methyl-3-trifluoromethylphenyl) anthranilate with approximately 10% of the required amount of water and pass through a suitable colloid millunitl free of grittiness. Add the milled active slurry to the batch. Dissolve the menthol and flavor in the alcohol and add the resulting solution to the batch. Add sufficient purified water to bring the batch to total volume. Agitate until uniform.

If desired, the compounds may also be co-administered with other previously utilized anti-diarrheal compositions (e.g. polycarbophil) although use of such other compositions is not necessary, the compounds of this invention being very effective in their anti-diarrheal use.

We claim:

1. The method for the treatment and control of diarrhea which comprises administering to a mammal suffering from diarrhea a therapeutically effective quantity of an N-aryl-anthranilic acid of the formula:

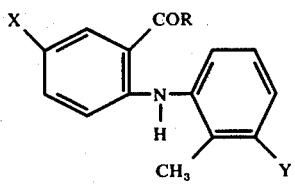

and the pharmaceutically acceptable salts thereof, wherein Y represents trifluoromethyl, difluoromethyl, or nitro, X represents hydrogen, bromo, chloro or nitro, and R represents OH, -O-lower alkyl, O-CH$_2$CHOHCH$_2$OH, O-alkyl-NR$_1$R$_2$, NHOH or NR$_1$NR$_2$, wherein R$_1$ and R$_2$ are each hydrogen or lower alkyl.

2. The method of claim 1 wherein R is OH.

3. The method of claim 1 wherein the ester is glyceryl.

4. The method of claim 1 wherein X is hydrogen, Y is trifluoromethyl and R is O-CH$_2$CHOHCH$_2$OH, said compound being glyceryl N-(2-methyl-3-trifluoromethylphenyl) anthranilate.

5. The method of claim 1 wherein X is bromo, Y is trifluoromethyl and R is O-CH$_2$CHOHCH$_2$OH, said compound being glyceryl 5-bromo-N-(2-methyl-3-trifluoromethylphenyl) anthranilate.

6. The method of claim 1 wherein x is bromo, Y is difluoromethyl and R is OH, said compound being 5-bromo-N-(2-methyl-3-difluoromethylphenyl) anthranilic acid.

7. The method of claim 1, wherein R represents a hydrazide.

8. The method according to claim 1 for the treatment and control of diarrhea in horses, wherein the condition is caused by an infection by Colitis X.

9. The method according to claim 1 for the treatment and control of diarrhea wherein the diarrhea has been caused by cholera.

10. The method according to claim 1 for the treatment and control of diarrhea in piglets, wherein the diarrhea is caused by the condition known as scours.

11. The compounds of the formula:

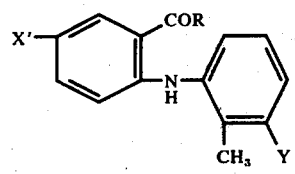

and the pharmaceutically acceptable salts thereof, wherein X' is H, chloro, bromo or nitro, Y is trifluoromethyl, difluoromethyl, or nitro, and R represents OH,-O-lower alkyl O-CH$_2$CHOHCH$_2$OH, NHOH, -O-alkyl NR$_1$R$_2$, or NR$_1$Nr$_2$, wherein R$_1$ and R$_2$ are each hydrogen or lower alkyl, with the proviso that when X' is hydrogen, Y is difluoromethyl.

12. The compounds of claim 11 wherein R represents the glyceryl ester.

13. The compounds of claim 11 wherein X' is bromo and Y is CF$_3$, R is OH, said compound being 5-bromo-N-(2-methyl-3-trifluoromethylphenyl) anthranilic acid.

14. The glyceryl ester of the compound of claim 13.

* * * * *